United States Patent
Schindler et al.

(10) Patent No.: US 6,180,637 B1
(45) Date of Patent: Jan. 30, 2001

(54) 1,2,5-TRISUBSTITUTED 1,2-DIHYDROINDAZOL-3-ONES HAVING ANTI-ASTHMATIC, ANTI-ALLERGIC, ANTI-INFLAMMATORY, IMMUNOMODULATING AND NEUROPROTECTIVE ACTION, PROCESS FOR THEIR PREPARATION AND THEIR USE AS MEDICAMENTS

(75) Inventors: Rudolf Schindler, Dresden; Norbert Höfgen, Medingen; Hildegard Poppe, Dresden; Kay Brune, Marloffstein, all of (DE)

(73) Assignee: Arzneimittelwerk Dresden GmbH (DE)

( * ) Notice: Under 35 U.S.C. 154(b), the term of this patent shall be extended for 0 days.

(21) Appl. No.: 09/305,602

(22) Filed: May 5, 1999

(30) Foreign Application Priority Data

May 11, 1998 (DE) .............................. 198 21 003

(51) Int. Cl.$^7$ ................ A61K 31/513; A61K 31/4152; C07D 231/56
(52) U.S. Cl. .................. 514/259; 514/259; 514/254.09; 514/365; 514/405; 546/275.7; 546/153; 544/235; 544/144; 544/284; 544/298; 544/333; 544/371; 548/131; 548/159; 548/181; 548/240; 548/305.1; 548/306.7; 548/361.5
(58) Field of Search ................ 548/361.5, 131, 548/159, 181, 240, 305.1, 306.7; 514/405, 259, 245.06, 365; 546/275.7, 153; 544/235, 371, 298, 284, 144, 333

(56) References Cited

U.S. PATENT DOCUMENTS

| | | | |
|---|---|---|---|
| 4,537,975 | 8/1985 | Heinemann et al. | 548/359 |
| 5,173,496 | * 12/1992 | Bruneau et al. | 514/338 |
| 5,179,112 | * 1/1993 | Bernstein et al. | 514/359 |
| 5,229,408 | * 7/1993 | Bruneau | 514/405 |

FOREIGN PATENT DOCUMENTS

| | | |
|---|---|---|
| 72961 | 3/1983 | (EP) . |
| 284174 | 9/1988 | (EP) . |
| 355970 | 2/1990 | (EP) . |
| WO 97/34874 | 9/1997 | (WO) . |

OTHER PUBLICATIONS

M. S. Malamas et al., Quinazolineacetic Acids, etc., J. Med. Chem. 1991, 34, 1492–1503.
R. Schindler et al., 1,5–Disubstituted Indazol etc., Arch. Pharm. Pharm. Med. Chem., 331, 13–21 (1998).
V. J. Aran, et al., Analogues of Cytostatic, etc., Liebigs Ann., 1996, 683–691.
G. Palazzo et al., Synthesis and Pharmacological Prop., vol. 9, Jan. 1996, 38–41.
M. H. Norman et al., Cyclic Benzamides as Mixed Dopamine, etc., J. Med. Chem., 1994, 37, 2552–2563.

* cited by examiner

Primary Examiner—Cecilia Tsang
Assistant Examiner—Sonya N Wright
(74) Attorney, Agent, or Firm—Gabriel P. Katona L.L.P.

(57) ABSTRACT

The invention relates to 1,2,5-trisubstituted 1,2-dihydroindazol-3-ones of formula (I)

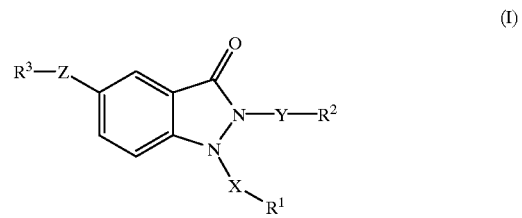

wherein
X is —$SO_2$—, —SO—, —$(CH_2)_p$—, —$(CH_2)_p$—O—, —$(CH_2)_p$—(C=O)—, —$(CH_2)_p$—(C=O)—NH—, —$(CH_2)_p$—CHOH—, —CHOH—$(CH_2)_p$—, —$(CH_2)_p$—CH=CH—, —CH=CH—$(CH_2)_p$—,
Y is —(C=O)—, —(C=O)—NH—, —(C=O)—NH—$(CH_2)_p$—, —(C=O)—$(CH_2)_p$—, —$(CH_2)_p$—, —$(CH_2)_p$—O—, —$(CH_2)_p$—(C=O)—, —$(CH_2)_p$—(C=O)—NH—, —$(CH_2)_p$—(C=O)—NH—$(CH_2)_p$—, —$(CH_2)_p$—CHOH—, —CHOH—$(CH_2)_p$—, —$(CH_2)_p$—CH=CH—, —CH=CH—$(CH_2)_p$—,
Z is —O—, —O—$(CH_2)_p$—, —NH—, —NH—(C=O)—, —NH—(C=O)—NH—, —NH—(C=O)—O—, —NH—$CH_2$—(C=O)— and —NH—(C=O)—$CH_2$—,
P is a cardinal number from 1 to 4,
$R^1$, $R^2$ and $R^3$ can be the same or different and are:
mono-, bi- or tricyclic saturated or mono- or polyunsaturated carbocycles having from 5 to 14 ring members; or mono-, bi- or tricyclic saturated or mono- or polyunsaturated heterocycles having from 5 to 15 ring members and from 1 to 6 heteroatoms,
in which the carbocycles and the heterocycles can be mono- or polysubstituted by:
$C_{1-6}$-alkyl, —O—$C_{1-6}$-alkyl, —O—$C_{3-7}$-cycloalkyl, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms,
$R^1$ is also H, provided that when X is $CH_2$, then $R^1$ is not H,
$R^3$—Z is also $NO_2$,
and their pharmaceutically acceptable salts,
but excluding compounds of formula (I) in which
if Z is —NH—(C=O)—, —NH—(C=O)—NH—, —NH—(C=O)—O—, —NH—(C=O)—$CH_2$ and at the same time $R^1$ is phenyl, monosubstituted or polysubstituted by —COOH, —COO$C_{1-6}$-alkyl, —$(CH_2)_p$—COOH, —$(CH_2)_p$—COO$C_{1-6}$-alkyl —CONH$C_{1-6}$-alkyl, —CONH$C_{6-14}$-aryl, —CONHSO$_2C_{1-6}$-alkyl, —CONHSO$_2C_{6-4}$-aryl, 1H-tetrazol-5-yl, then $R^2$ is not phenyl, monosubstituted or polysubstituted by CN, halogen, $C_{1-4}$-alkyl, $C_{1-4}$-alkyloxy, $CF_3$; and
if $R^3$—Z is $NO_2$, then $R^1$—X is not benzyl or 4-methoxybenzyl, and $R^2$—Y is not benzyl or 2-picolyl at the same time; and to pharmaceutical treatment processes, and processes for making.

12 Claims, No Drawings

1,2,5-TRISUBSTITUTED 1,2-DIHYDROINDAZOL-3-ONES HAVING ANTI-ASTHMATIC, ANTI-ALLERGIC, ANTI-INFLAMMATORY, IMMUNOMODULATING AND NEUROPROTECTIVE ACTION, PROCESS FOR THEIR PREPARATION AND THEIR USE AS MEDICAMENTS

New 1,2,5-trisubstituted 1,2-dihydroindazol-3-ones having anti-asthmatic, anti-allergic, anti-inflammatory, immunomodulating and neuroprotective action, process for their preparation and their use as medicaments.

TECHNICAL FIELD

The invention relates to the preparation and use of novel derivatives of indazol-3-one as medicaments having anti-asthmatic, anti-allergic, anti-inflammatory, immunomodulating and neuroprotective properties.

PRIOR ART

Cyclosporin A (CsA) and FK 506 are immunosuppressant natural substances originating from fungi, which inhibit the $Ca^{2+}$-dependent signal transmission pathway in some cell types. In T cells, both compounds inhibit the transcription of a number of genes. CsA and FK-506 both bind with high affinity to soluble receptor proteins such as, for example, cyclophilin (Cyp) or FK-506 binding protein (FKBP) (G. Fischer et al., Nature 337 (1989), 476–478; M. W. Harding et al., Nature 341 (1989), 755–760).

The complex of CsA-Cyp or FK 506-FKBP binds calcineurin (CN) and inhibits its phosphatase activity. The cytosolic, phosphorylating component of the transcription factor NF-AT was recognized as a cellular target molecule of CN, so that in the absence of CN activity the active transcription complex on the IL 2 promoter cannot be switched on (M. K. Rosen, S. L. Schreiber, Angew. Chem. 104 (1992), 413–430; G. Fischer, Angew. Chem. 106 (1994), 1479–1501).

The allergic, asthmatic diseases are based on an inflammatory reaction which is controlled by T cells and their mediators. Corticosteroids are still the agent of choice in the treatment of many allergic diseases. CsA and FK 506 also proved to be a favourable therapeutic in bronchial asthma and underlying inflammations both in animal experiments and in clinical studies.

Despite the large number of attempts at the identification of new active immunophilin inhibitors, until now it was not possible to prepare or isolate any more active structures than CsA, FK 506, rapamycin or derivatives of these natural substances. The high inhibitory potential of CsA, FK 506 and rapamycin, however, is very considerably reduced by the various side effects, in particular the nephrotoxicity (N. H. Sigal et al., J. Exp. Med. 173 (1991), 619–6128). What is behind this fact is the non-specificity of the interaction between immunophilin ligands and the cell-specific binding proteins. As a result, the known medicinal-therapeutic action of these immuno-suppressants is considerably restricted. Furthermore, the lacking selectivity of the compounds proves to be problematic especially in long-term therapy.

Substances which inhibit the activity of peptidylprolyl isomerases (PPIases) such as Cyp or FKBP, have neuroprotective properties, stimulate neuronal growth and are suitable for the treatment of neurodegenerative diseases (WO 96/40140, U.S. Pat. No. 5,696,135, WO 97/18828).

Substituted indazole derivatives are known which, however, differ from the claimed compounds with respect to the substituents X, Y, Z, $R^1$, $R^2$ and $R^3$ and their pharmacodynamic action.

Baiocchi et al. [Synthesis 1978 (9), 633–648] give a general survey of syntheses and properties of the 1,2-dihydro-3H-indazol-3-ones.

Schindler et al. [WO 97/34874] describe 1,3,5-trisubstituted indazoles having anti-asthmatic, anti-allergic, anti-inflammatory and immunomodulating action.

EP 0 199 543 includes 1,6-disubstituted 1,2-dihydroindazol-3-ones and their use for pharmaceutical purposes.

WO 94/24109 includes indazole derivatives which are suitable for the treatment of HIV infections.

Ketami et al. [J. Heterocycl. Chem. 7 (4), 807–813 (1970)] describe 1,5-disubstituted 1,2-dihydroindazol-3-ones.

U.S. Pat. No. 3,470,194 mentions the formation of disubstituted (1,2-dihydro-3-oxyindazol-2-yl)alkanoic acids when using polar solvents.

K. v. Auwers [Ber. Dtsch. Chem. Ges. 58, 2081–2088 (1925)] and K. v. Auwers et al. [Justus Liebigs Ann. Chem. 451, 281–307 (1927)] describe the constitution of acylindazoles and their migration.

Zoni et al. [Il Farmaco Ed. Sci. 23 (5), 490–501 (1968)] and Zoni et al. [Boll. Chim. Farm. 107, 598–605 (1968)] describe the alkylation of 1-substituted 1H-indazol-3-ols.

Evans et al. [Tetrahedron 21, 3351–3361 (1965)] describe the synthesis of 1,3-substituted acyl- and tosylindazoles.

Tse et al. [Arch. Pharm. 329 (1), 35–40 (1996)] report on anti-inflammatory properties of N-substituted indazoles.

Anderson et al. [J. Chem. Soc. C, 3313–3314 (1971)] describe 1,3-substituted tosylindazoles.

Palazzo et al. [J. Med. Chem 9, 38–41 (1996)] and Gyula et al. [Acta pharm. Hung. 44, 49–57 (1974)] describe the synthesis of 2-dimethylaminoalkyl-1-phenylindazol-3-ones.

Klicnar [Coll. Czech. Chem. Comm. 42, 327–337 (1977)] describes acetylindazoles.

Tserng et al. [J. Org. Chem. 38, 3498–3502 (1973)] describe the synthesis of 1,2-disubstituted 1,2-dihydroindazol-3-ones.

Aran et. al. [Heterocycles 45, 129–136 (1997)] describe the selective synthesis of 2-substituted indazol-3-ones without N-1 substitution.

Aran et al. [Liebigs Ann. 1996, 683–691], Aran et al. [Liebigs Ann. 1995, 817–824] and Aran et al. [J. Chem. Soc. Perkin Trans. I, 1119–1127 (1993)] describe 1,2-substituted 5-nitroindazol-3-ones and their -cytostatic activity.

Bruneau et al. [J. Med. Chem. 34, 1028–1036 (1991)] describe 1- and 2-substituted indazol-3-ones as 5-lipoxygenase inhibitors.

Wyrick et al. [J. Med. Chem. 27, 768–772 (1984)] describe 1,2-disubstituted indazol-3-ones having cholesterol-lowering action.

Schmutz et al. [Helv. Chim. Acta 47, 1986–1996 (1964)] describe the alkylation of indazolones.

Yamaguchi et al. [Chem. Pharm. Bull. 43 (2), 332–334 (1995)] describe 2-substituted (1-pyridin-3-yl)indazol-3-ones and their anti-asthmatic action.

On account of numerous side effects of the preparations introduced, lack of curative effects and the hitherto too non-specific therapy, a great need for compounds having a high effectiveness and safety furthermore exists for the treatment of asthmatic diseases.

The invention is based on the object of finding new compounds having rotamase-inhibiting and/or pulmonary eosinophil infiltration-inhibiting properties and making them available by targeted synthesis.

A completely novel class of substance, which surprisingly binds immunophilins specifically, is represented by the compounds of the formula I according to the invention. This class of compounds has a high affinity for immunophilins such as CypB.

DESCRIPTION OF THE INVENTION

Surprisingly, it has now been found that the new indazole derivatives are able to inhibit the action of PPIase. Accordingly, these compounds are of great importance for the production of medicaments where the inhibition of PPIase is of benefit. Such illnesses are, for example: peripheral neuropathies, neurodegeneration, stroke, Parkinson's and Alzheimer's diseases, traumatic brain diseases, multiple sclerosis.

It has furthermore been demonstrated that the compounds according to the invention are able to inhibit the infiltration of eosinophilic granulocytes into the tissue, which is characteristic of the asthmatic late-phase reaction.

The invention relates to new 1,2,5-trisubstituted 1,2-dihydroindazol-3-ones of the general formula I

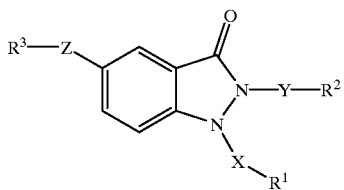

Formula I in which X, Y, Z, $R^1$, $R^2$ and $R^3$ have the following meaning:
X can be —$SO_2$—, —SO—, —$(CH_2)_p$—, —$(CH_2)_p$—O—, —$(CH_2)_p$—(C=O)—, —$(CH_2)_p$—(C=O)—NH—, $(CH_2)_p$—CHOH—; —CHOH—$(CH_2)_p$—, —$(CH_2)_p$—CH=CH—, —CH=CH—$(CH_2)_p$— where p=1 . . . 4,
Y can be —(C=O)—, —(C=O)—NH—, —(C=O)—NH—$(CH_2)_p$—, —(C=O)—$(CH_2)_p$—, —$(CH_2)_p$—, —$(CH_2)_p$—O—, —$(CH_2)_p$—(C=O)—, —$(CH_2)_p$—(C=O)—NH—, —$(CH_2)_p$—(C=O)—NH—$(CH_2)_p$—, —$(CH_2)_p$—CHOH—, —CHOH—$(CH_2)_p$—, —$(CH_2)_p$—CH=CH—, —CH=CH—$(CH_2)_p$—where p=1 . . . 4,
Z can be —O—, —O—$(CH_2)_p$— where p=1 . . . 4, —NH—, —NH—(C=O)—, —NH—(C=O)—NH—, —NH—(C=O)—O—, —NH—$CH_2$—(C=O)—and —NH—(C=O)—$CH_2$—,
$R^1$, $R^2$ and $R^3$ can be identical or different and have the following meaning:
mono-, bi- or tricyclic saturated or mono- or polyunsaturated carbocycles having 5 . . . 14 ring members, in particular phenyl, naphthyl, anthranyl, fluorenyl; or mono-, bi- or tricyclic saturated or mono- or polyunsaturated heterocycles having 5 . . . 15 ring members and 1 . . . 6 heteroatoms, which are preferably N, O and S, in particular thiophenyl, pyridinyl, isoxazolyl, benzimidazolyl, benzo[1,3]dioxolyl, pyrimidinyl, quinolyl, quinazolinyl, morpholinyl, pyrrolidinyl, pyrrolyl, benz[1,2,4]oxadiazolyl, benzothiazolyl,
where the carbocycles and the heterocycles can be mono- or polysubstituted by:
—$C_{1 \ldots 6}$-alkyl, —O—$C_{1 \ldots 6}$-alkyl, —O—$C_{3 \ldots 7}$-cycloalkyl, mono-, bi- or tricyclic saturated or mono- or polyunsaturated carbocycles having 3 . . . 14 ring members, mono-, bi- or tricyclic saturated or mono- or polyunsaturated heterocycles having 5 . . . 15 ring members and 1 . . . 6 heteroatoms, which are preferably N, O and S, —F, —Cl, —Br, —I, —OH, —SH, —$NO_2$, —$NH_2$, —$NHC_{1 \ldots 6}$-alkyl, —$N(C_{1 \ldots 6}$-alkyl$)_2$, —$NHC_{6 \ldots 14}$-aryl, —$N(C_{6 \ldots 14}$-aryl$)_2$, —$N(C_{1 \ldots 6}$-alkyl)—$(C_{6 \ldots 14}$-aryl), —$NHCOC_{1 \ldots 6}$-alkyl, —$NHCOC_{6 \ldots 14}$-aryl, —$CONHC_{1 \ldots 6}$-alkyl, —$CONHC_{6 \ldots 14}$-aryl, —$CONHSO_2C_{1 \ldots 6}$-alkyl, —$CONHSO_2C_{6 \ldots 14}$-aryl, —CN, —(CO)$C_{1 \ldots 6}$-alkyl, —(CS)$C_{1 \ldots 6}$-alkyl, —COOH, —$COOC_{1 \ldots 6}$-alkyl, —O—$C_{6 \ldots 14}$-aryl, —O—(CO)$C_{1 \ldots 6}$-alkyl, —O—(CO)$C_{6 \ldots 14}$-aryl, benzyl, benzyloxy, —S—$C_{1 \ldots 6}$-alkyl, —S—$C_{6 \ldots 14}$-aryl, —$CF_3$, —$(CH_2)_p$—COOH where p=1 to 4, —$(CH_2)_p$-$COOC_{1 \ldots 6}$-alkyl where p=1 to 4, —$SO_2$—$C_{1 \ldots 6}$-alkyl, —$SO_2$—$C_{6 \ldots 14}$-aryl,
$R^1$ can furthermore be H (but not if X=$CH_2$),
$R^3$—Z can furthermore be $NO_2$.
The compounds according to the invention are new, but excluding compounds as in formula I:
if Z is —NH—(C=O)—, —NH—(C=O)—NH—, —NH—(C=O)—O—, —NH—(C=O)—$CH_2$— and simultaneously $R^1$=phenyl, monosubstituted or polysubstituted by —COOH, —$COOC_{1 \ldots 6}$-alkyl, —$(CH_2)_p$—COOH, where p=1 to 4, —$(CH_2)_p$—$COOC_{1 \ldots 6}$-alkyl where p=1 . . . 4, —$CONHC_{1 \ldots 6}$-alkyl, —$CONHC_{6 \ldots 14}$-aryl, —$CONHSO_2C_{1 \ldots 6}$-alkyl, —$CONHSO_2C_{6 \ldots 14}$-aryl, 1H-tetra-zol-5-yl, then $R^2$ must not be phenyl, monosubstituted or polysubstituted by CN, halogen, $C_{1 \ldots 4}$-alkyl, $C_{1 \ldots 4}$-alkyloxy, $CF_3$;
if $R^3$—Z=$NO_2$, then $R^1$—X and $R^2$—Y must not simultaneously have the following meaning:
$R^1$—X=benzyl, 4-methoxybenzyl
$R^2$—Y=benzyl, 2-picolyl.
The invention furthermore relates to the physiologically tolerable salts of the compounds according to formula I.

The pharmacologically tolerable salts are obtained in a customary manner by neutralization of the bases with inorganic or organic acids or by neutralization of the acids with inorganic or organic bases. Possible inorganic acids are, for example, hydrochloric acid, sulphuric acid, phosphoric acid or hydrobromic acid, organic acids are, for example, carboxylic, sulpho or sulphonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Possible inorganic bases are, for example, sodium hydroxide solution, potassium hydroxide solution, ammonia and organic bases are amines, preferably, however, tertiary amines, such as trimethylamine, triethylamine, pyridine, N,N-dimethylaniline, quinoline, isoquinoline, α-picoline, β-picoline, γ-picoline, quinaldine or pyrimidine.

In addition, physiologically tolerable salts of the compounds according to formula I can be obtained by converting derivatives which have tertiary amino groups into the corresponding quaternary ammonium salts in a manner known per se. Possible quaternizing agents are, for example, alkyl halides such as methyl iodide, ethyl bromide and n-propyl chloride, but also arylalkyl halides such as benzyl chloride or 2-phenylethyl bromide.

Furthermore, the invention of compounds of the formula I which contain an asymmetric carbon atom relates to the D form, the L form and D,L mixtures and, in the case of a number of asymmetric carbon atoms, the diastereomeric forms. Those compounds of the formula I which contain asymmetric carbon atoms and are obtained as a rule as racemates, can be separated into the optically active isomers in a manner known per se, for example using an optically active acid. However, it is also possible to employ an optically active starting substance from the beginning, a corresponding optically active or diastereomeric compound then being obtained as a final product.

The invention relates to the preparation and use of the compounds according to the invention or their physiologically tolerable salts as 1. inhibitors of rotamases for the production of medicaments for the treatment of diseases mediated by this enzyme and/or
2. inhibitors of late-phase eosinophilia for the production of medicaments for the treatment of diseases mediated by these cells.

These diseases include, for example, peripheral neuropathies, neurodegeneration, stroke, Parkinson's and Alzheimer's diseases, traumatic brain diseases, multiple sclerosis, bronchial asthma, allergic rhinitis, allergic conjunctivitis, atopic dermatitis, eczema, allergic angiitis, inflammations mediated by eosinophils such as eosinophilic fasciitis, eosinophilic pneumonia and PIE syndrome, autoimmune diseases such as rheumatoid arthritis, rheumatoid spondylitis, lupus erythematosus, psoriasis, glomerulonephritis and uveitis, insulin-dependent diabetes mellitus and sepsis.

The compounds according to the invention or their physiologically tolerable salts are furthermore used for the production of medicaments for the prevention of rejection reactions after transplantation of cells, tissues or organs.

For the production of the medicaments, in addition to the customary auxiliaries, carriers and additives, an efficacious dose of the compounds according to the invention or their salts is used.

The dose of the active compounds can vary depending on the administration route, age, weight of the patient, nature and severity of the diseases to be treated and similar factors.

The daily dose can be given as an individual dose to be administered once or subdivided into 2 or more daily doses and is, as a rule, 0.001–1000 mg.

Possible administration forms are oral, parenteral, intravenous, transdermal, topical, inhalational and intranasal preparations.

For administration, possible customary pharmaceutical preparation forms are those such as tablets, coated tablets, capsules, dispersible powders, granules, aqueous solutions, aqueous or oily suspensions, syrup, juices or drops.

Solid pharmaceutical forms can contain inert ingredients and carriers, such as, for example, calcium carbonate, calcium phosphate, sodium phosphate, lactose, starch, mannitol, alginates, gelatin, guar gum, magnesium or aluminium stearate, methylcellulose, talc, highly disperse silicic acids, silicone oil, high molecular weight fatty acids (such as stearic acid), gelatin, agar-agar or vegetable or animal fats and oils, solid high molecular weight polymers (such as polyethylene glycol); preparations suitable for oral administration can contain, if desired, additional flavourings and/or sweeteners.

Liquid pharmaceutical forms can be sterilized and/or optionally contain auxiliaries such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Additives of this type are, for example, tartrate and citrate buffers, ethanol, complexing agents (such as ethylenediaminetetraacetic acid and its non-toxic salts). For regulating the viscosity, possible high molecular weight polymers are those such as, for example, liquid polyethylene oxide, microcrystalline celluloses, carboxymethylcelluloses, polyvinylpyrrolidones, dextrans or gelatin. Solid carriers are, for example, starch, lactose, mannitol, methylcellulose, talc, highly disperse silicic acids, high molecular weight fatty acids (such as stearic acid), gelatin, agar-agar, calcium phosphate, magnesium stearate, animal and vegetable fats, solid high molecular weight polymers such as polyethylene glycol.

Oily suspensions for parenteral or topical application can be vegetable synthetic or semi-synthetic oils such as, for example, liquid fatty acid esters in each case having 8 to 22 C atoms in the fatty acid chains, for example palmitic, lauric, tridecylic, margaric, stearic, arachic, myristic, behenic, pentadecanoic, linoleic, elaidic, brassidic, erucic or oleic acid, which are esterified with mono- to trihydric alcohols having 1 to 6 C atoms, such as, for example, methanol, ethanol, propanol, butanol, pentanol or their isomers, glycol or glycerol. Fatty acid esters of this type are, for example, commercially available Miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters such as artificial duck preen gland fat, isopropyl cocoate, oleyl oleate, decyl oleate, ethyl lactate, dibutyl phthalate, diisopropyl adipate, polyol fatty acid esters and others. Also suitable are silicone oils of differing viscosities or fatty alcohols such as isotridecyl alcohol, 2-octyldodecanol, cetylstearyl alcohol or oleyl alcohol, fatty acids such as, for example, oleic acid. It is furthermore possible to use vegetable oils such as castor oil, almond oil, olive oil, sesame oil, cottonseed oil, groundnut oil or soya bean oil.

Possible solvents, gelling agents and solubilizers are water or water-miscible solvents. Those suitable are, for example, alcohols such as, for example, ethanol or isopropyl alcohol, benzyl alcohol, 2-octyldodecanol, polyethylene glycols, phthalates, adipates, propylene glycol, glycerol, di- or tripropylene glycol, waxes, methylcellosolve, cellosolve, esters, morpholines, dioxane, dimethyl sulphoxide, dimethylformamide, tetrahydrofuran, cyclohexanone etc.

Film-forming agents which can be used are cellulose ethers which can dissolve or swell both in water and in organic solvents, such as, for example, hydroxypropylmethylcellulose, methylcellulose, ethylcellulose or soluble starches.

Mixed forms between gel- and film-forming agents are also perfectly possible. Here, especially, ionic macromolecules are used, such as, for example, sodium carboxymethylcellulose, polyacrylic acid, polymethacrylic acid and its salts, sodium amylopectin semiglycolate, alginic acid or propylene glycol alginate as the sodium salt, gum arabic, xanthan gum, guar gum or carrageenan.

Further formulation auxiliaries which can be employed are: glycerol, paraffin of differing viscosities, triethanolamine, collagen, allantoin, novantisolic acid.

The use of surfactants, emulsifiers or wetting agents can also be necessary for formulation, such as, for example, of Na laurylsulphate, fatty alcohol ether sulphates, di-Na N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenyl polyglycol ethers, cetyltrimethylammonium chloride or mono-/dialkyl polyglycol ether orthophosphoric acid monoethanolamine salts.

Stabilizers such as montmorillonites or colloidal silicic acids for the stabilization of emulsions or for -the prevention of the breakdown of the active substances, such as antioxidants, for example tocopherols or butylhydroxyanisole, or preservatives, such as p-hydroxybenzoic acid esters, can also be necessary for the preparation of the desired formulations.

The preparation, dispensation and sealing of the preparations is carried out under the customary antimicrobial and aseptic conditions.

The dose of the pharmaceutical preparations depends on the age, condition and weight of the patient and on the administration form. As a rule, the daily dose of active compound is between 0.001 and 25 mg/kg of body weight.

Preparation

According to the present invention, the compounds of the general formula I can be prepared by the following processes:

Process for the preparation of the compounds of the general formula I, characterized in that a) for X=—$SO_2$—, —SO— the reaction is carried out according to scheme 1.

1H-Indazol-3-yl sulphonates II are reacted in the presence of a base and if appropriate in the presence of a diluent to give compounds of the general formula III, where $R^1$, $R^3$, X and Z have the abovementioned meaning.

1H-Indazol-3-yl sulphonates II or 1-sulphonylindazoles III are reacted, if appropriate in the presence of a base, in particular sodium hydride, and if appropriate in the presence of a diluent, in particular dimethyl sulphoxide, with compounds of the following general formulae Hal-Y-$R^2$, O=C=N—$(CH_2)_p$—$R^2$, [$R^2$—$(CH_2)_p$—C=O]$_2$O with p=0 . . . 5, where $R^1$, $R^2$, $R^3$, X, Y and Z have the abovementioned meaning and Hal is a halogen atom F, Cl, Br or iodine, to give compounds of the general formula I, where $R^1$, $R^2$, $R^3$, X, Y and Z have the abovementioned meaning.

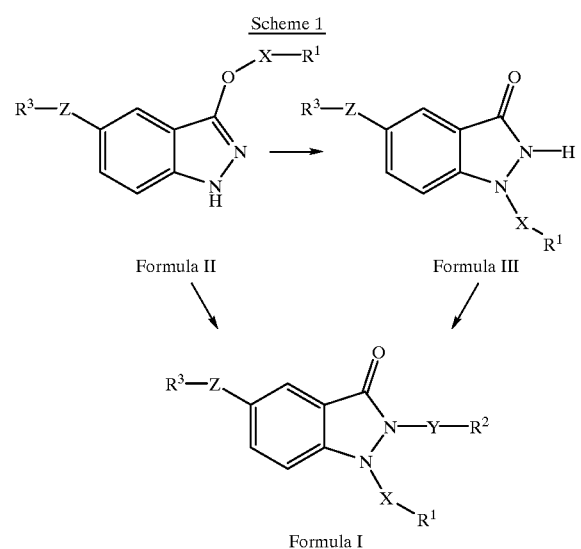

Formula II   Formula III

Formula I b) for X—$(CH_2)_p$—, —$(CH_2)_p$—O—, —$(CH_2)_p$—(C=O)—, —$(CH_2)_p$—(C=O)—NH—, —$(CH_2)_p$—CHOH—, —CHOH—$(CH_2)$—, —$(CH_2)_p$—CH=CH—, —CH=CH—$(CH_2)_p$— where p=1 . . . 4 the reaction is carried out according to scheme 2.

Compounds of the general formula III are reacted, if appropriate in the presence of a base, in particular pyridine or sodium hydride, and if appropriate in the presence of a diluent, in particular tetrahydrofuran or dimethyl sulphoxide, with compounds of the following general formulae Hal-Y-$R^2$, O=C=N—$(CH_2)_p$—$R^2$, [$R^2$—$(CH_2)_p$—C=O]$_2$O with p=0 . . . 5, where $R^1$, $R^2$, $R^3$, X, Y and Z have the abovementioned meaning and Hal is a halogen atom F, Cl, Br or iodine, to give compounds of the general formula I, where $R^1$, $R^2$, $R^3$, X, Y and Z have the abovementioned meaning.

Scheme 2

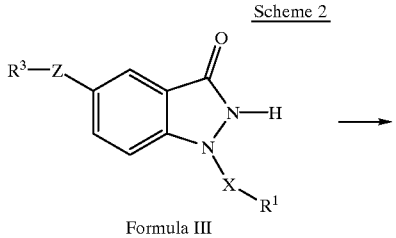

Formula III

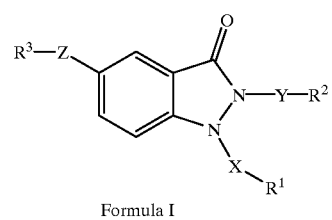

Formula I where formula III can also be present as the tautomeric form formula IV according to scheme 3.

Scheme 3

Formula III   Formula IV

The compounds of the general formula I are new.

WORKING EXAMPLES

The following representatives of the compounds according to the invention are mentioned by way of example:

2-(2-hydroxy-5-nitrobenzyl)-5-methoxy-1-(4-methoxy-benzenesulphonyl)-1,2-dihydroindazol-3-one 2-(2-hydroxy-5-nitrobenzyl)-5-methoxy-1-(toluene-4-sulphonyl)-1,2-dihydroindazol-3-one 2-(2-hydroxy-5-nitrobenzyl)-5-methoxy-1-(4-trifluoro-methoxybenzenesulphonyl)-1,2-dihydroindazol-3-one 2-(2-hydroxy-5-nitrobenzyl)-5-methoxy-1-(4-chloro-benzenesulphonyl)-1,2-dihydroindazol-3-one 1-(4-fluorobenzenesulphonyl)-2-(2-hydroxy-5-nitrobenzyl)-5-methoxy-1,2-dihydroindazol-3-one N-(4-[2-(2-hydroxy-5-nitrobenzyl)-5-methoxy-3-oxo-2,3-dihydroindazol-1-sulphonyl]phenyl)acetamide 2-(4-fluorobenzyl)-5-methoxy-1-(toluene-4-sulphonyl)-1,2-dihydroindazol-3-one 2-(4-fluorobenzyl)-5-methoxy-1-(4-chlorobenzene-sulphonyl)-1,2-dihydroindazol-3-one 1-(4-fluorobenzenesulphonyl)-2-(4-fluorobenzyl)-5-methoxy-1,2-dihydroindazol-3-one 2-(2-fluorobenzyl)-5-methoxy-1-(toluene-4-sulphonyl)-1,2-dihydroindazol-3-one 1-(4-fluorobenzenesulphonyl)-2-(2-fluorobenzyl)-5-methoxy-1,2-dihydroindazol-3-one 2-(3-methoxybenzyl)-5-methoxy-1-(toluene-4-sulphonyl)-1,2-dihydroindazol-3-one 2-(3-trifluoromethylbenzyl)-5-methoxy-1-(toluene-4-sulphonyl)-1,2-dihydroindazol-3-one 2-[2-(4-chlorophenyl)thiazol-4-ylmethyl]-5-methoxy-1-(toluene-4-sulphonyl)-1,2-dihydroindazol-3-one 5-methoxy-2-(3-phenylallyl)-1-(toluene-4-sulphonyl)-1,2-dihydroindazol-3-one 5-methoxy-2-(3-oxo-3-phenylpropyl)-1-(toluene-4-sulphonyl)-1,2-dihydroindazol-3-one 2-[2-(2,6-difluorophenoxy)ethyl]-5-methoxy-1-(toluene-4-sulphonyl)-1,2-dihydroindazol-3-one 2-[2-(2-bromo-4,6-difluorophenoxy)ethyl]-5-methoxy-1-(toluene-4-sulphonyl)-1,2-dihydroindazol-3-one 2-[2-(2-bromo-4,6-difluorophenoxy)ethyl]-5-methoxy-1-(4-methoxybenzenesulphonyl)-1,2-dihydroindazol-3-one N-(4-{2-[2-(2,4-dioxo-1,4-dihydro-2H-quinazolin-3-yl)ethyl]-5-methoxy-3-oxo-2,3-dihydroindazol-1-sulphonyl}phenyl)acetamide 2-{3-[4-(3-chlorophenyl)piperazin-1-yl]propyl}-5-methoxy-1-(toluene-4-sulphonyl)-1,2-dihydroindazol-3-one 1-(4-chlorobenzenesulphonyl)-2-{3-[4-(3-chlorophenyl)piperazin-1-yl]propyl}-5-methoxy-1-(toluene-4-sulphonyl)-1,2-dihydroindazol-3-one N-benzyl-2-[5-methoxy-3-oxo-1-(toluene-4-sulphonyl)-1,3-dihydroindazol-2-yl]acetamide 2-[5-methoxy-3-oxo-1-(toluene-4-sulphonyl)-1,3-dihydroindazol-2-yl]-N-(4-methoxyphenyl)acetamide 2-(2,6-dichlorobenzoyl)-5-nitro-1-(toluene-4-sulphonyl)-1,2-dihydroindazol-3-one 1-(3,4-dichlorobenzyl)-2-(2-hydroxy-5-nitrobenzyl)-5-methylthio-1,2-dihydroindazol-3-one 2-(2-hydroxy-5-nitrobenzyl)-5-methoxy-1-(3-nitrobenzyl)-1,2-dihydroindazol-3-one 5-methoxy-1-(3-nitrobenzyl)-3-oxo-1,3-dihydroindazol-2-carboxylic acid (2-fluorophenyl)amide 5-methoxy-1-(3-nitrobenzyl)-3-oxo-1,3-dihydroindazol-2-carboxylic acid (2,6-dichlorophenyl)amide 5-methoxy-1-(3-nitrobenzyl)-3-oxo-1,3-dihydroindazol-2-carboxylic acid (2-fluoro-6-trifluoromethylphenyl)amide methyl 3-[2-(2-fluorophenylcarbamoyl)-5-methoxy-3-oxo-2,3-dihydroindazol-1-ylmethyl]benzoate 1-(4-fluorobenzyl)-5-methoxy-3-oxo-1,3-dihydroindazole-2-carboxylic acid (2,6-dichlorophenyl)amide 4-nitrobenzyl 1-(4-fluorobenzyl)-5-methoxy-3-oxo-1,3-dihydroindazole-2-carboxylate 1-(2,6-difluorobenzyl)-5-methoxy-3-oxo-1,3-dihydroindazole-2-carboxylic acid (2,6-dichlorophenyl) amide 1-(2-chloro-6-fluorobenzyl)-5-methoxy-3-oxo-1,3-dihydroindazole-2-carboxylic acid (2,6-dichlorophenyl)-amide.

The compounds are characterized by means of melting point, thin-layer chromatography, elemental analysis, NMR spectroscopy, IR and UV-VIS spectroscopy and optionally using mass spectroscopy.

Purification using column liquid chromatography: In the preparation of the compounds of Examples 1 to 35, the 1- and 3-O-substituted 1H-indazoles according to the general formula V can be formed as by-products.

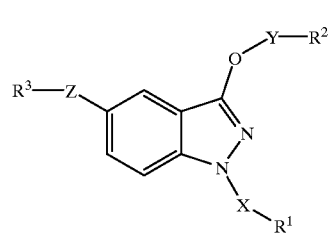

Formula V

The compounds of the general formula I can usually be separated from the compounds of the general formula V by recrystallization. If this is unsuccessful, a column-chromatographic separation under the following conditions is necessary: stationary phase: normal phase silica gel, e.g. Si 60 to 100 Å, particle size 5 to 100 μM. Eluent: methylene chloride/ethyl acetate=95/5 or methylene chloride/methanol=95/5.

The compounds of the general formula I are more polar than the compounds of the general formula V, so the compounds of the general formula I are eluted after the compounds of the general formula V under these chromatographic conditions. This purification operation is applicable to all of Examples 1 to 35.

Example 1

2-(2-Hydroxy-5-nitrobenzyl)-5-methoxy-1-(4-methoxybenzenesulphonyl)-1,2-dihydroindazol-3-one

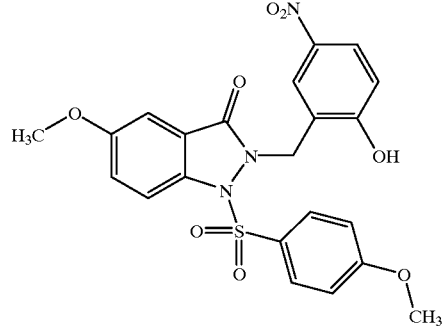

5.01 g (15 mmol) of 5-methoxy-1H-indazol-3-yl 4-methoxybenzenesulphonate are dissolved in 70 ml of DMSO and treated in portions with 1.5 g (37.5 mmol) of sodium hydride (60 percent). After stirring for 2 hours, a solution of 2.81 g (15 mmol) of 2-hydroxy-5-nitrobenzyl chloride in 25 ml of DMSO is added dropwise and the mixture is stirred at 90–100° C. for 3 hours. After cooling, 400 ml of water are added, and the mixture is stirred for 3 hours and extracted three times with 400 ml of ethyl acetate. The combined organic phases are washed with 100 ml of water, dried over sodium sulphate, distilled to dryness in vacuo and the residue is recrystallized from ethanol.

Yield: 3.0 g (41.1% of theory)

M.p. 215–217° C.

$^{13}$C NMR (DMSO-$d_6$; 300 MHZ): δ=46.0 $CH_2N$; 55.8 2×$CH_3O$; 165.1 C=O.

IR(KBr): ν=1669 cm$^{-1}$ C=O.

The compounds listed in Table 1 are prepared by an analogous procedure.

TABLE 1

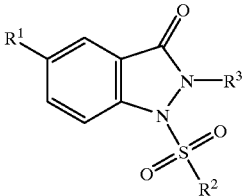

Formula VI $R^1 = CH_3O$

| Example | $R^2$ | $R^3$ | Yield (% of theory) | m.p. [° C.] | IR (KBr) [cm$^{-1}$] C=O | $^{13}$C—NMR (DMSO) N—CH$_2$ |
|---|---|---|---|---|---|---|
| 2 | 4-Tolyl | 2-hydroxy-5-nitrobenzyl (CH$_2$-C$_6$H$_3$(OH)(NO$_2$)) | 20 | 212–215 (2-PrOH) | 1673 | 46.62 |
| 3 | 4-Trifluoro-methoxyphenyl | 2-hydroxy-5-nitrobenzyl | 67 | 99–103 (EtOH) | 1694 | 46.81 |
| 4 | 4-Chlorophenyl | 2-hydroxy-5-nitrobenzyl | 66 | 212–216 (MeCN) | 1690 | 45.33 |
| 5 | 4-Fluorophenyl | 2-hydroxy-5-nitrobenzyl | 55 | 210–212 (EtOH) | 1690 | 46.54 |
| 6 | 4-Acetyl-aminophenyl | 2-hydroxy-5-nitrobenzyl | 25 | 242–244 (EtOH) | 1672; 1713 | 46.50 |
| 7 | 4-Tolyl | 4-fluorobenzyl (CH$_2$-C$_6$H$_4$-F) | 12 | 151 (MeOH) | 1703 | 48.89 |
| 8 | 4-Chlorophenyl | 4-fluorobenzyl | 8 | 179 (EtOH) | 1704 | 49.81 |

TABLE 1-continued
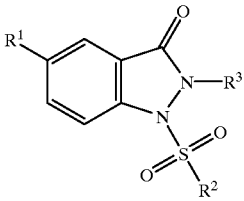
Formula VI
$R^1 = CH_3O$
| Example | $R^2$ | $R^3$ | Yield (% of theory) | m.p. [° C.] | IR (KBr) [cm$^{-1}$] C=O | $^{13}$C—NMR (DMSO) N—CH$_2$ |
|---|---|---|---|---|---|---|
| 9 | 4-Fluoro-phenyl | 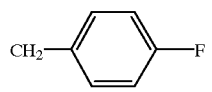 | 28 | 167–169 (EtOH) | 1708 | 49.53 |
| 10 | 4-Tolyl | 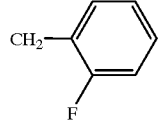 | 65 | 164–167 (2-PrOH) | 1712 | 44.54 |
| 11 | 4-Fluoro-phenyl | 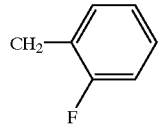 | 16 | 151–153 (MeCN) | 1713 | 49.36 |
| 12 | 4-Tolyl | 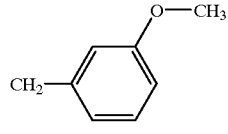 | 10 | 125–127 (MeCN) | 1704 | 47.77 |
| 13 | 4-Tolyl | 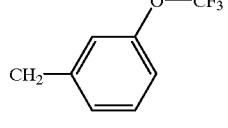 | 18 | 110 (EtOH) | 1704 | 49.86 |
| 14 | 4-Tolyl | 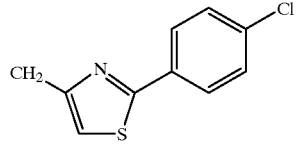 | 52 | 192–193 (MeCN) | 1703 | 47.14 |
| 15 | 4-Tolyl | 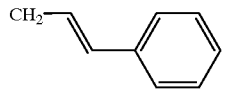 | 58 | 137–139 (2-PrOH) | 1708 | 46.22 |
| 16 | 4-Tolyl | 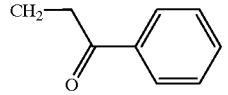 | 19 | 140–145 (EtOH) | 1690; 1716 | 41.20 |

TABLE 1-continued

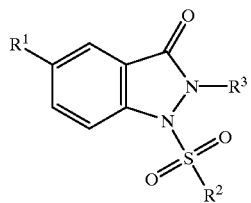

Formula VI $R^1 = CH_3O$

| Example | $R^2$ | $R^3$ | Yield (% of theory) | m.p. [° C.] | IR (KBr) [cm$^{-1}$] C=O | $^{13}$C—NMR (DMSO) N—CH$_2$ |
|---|---|---|---|---|---|---|
| 17 | 4-Tolyl | CH$_2$—O-(2,6-difluorophenyl) | 10 | 151–153 (EtOH) | 1718 | 46.99 |
| 18 | 4-Tolyl | CH$_2$—O-(2-bromo-4,6-difluorophenyl) | 7 | 125–125 (2-PrOH) | 1717 | 46.86 |
| 19 | 4-Methoxyphenyl | CH$_2$—O-(2-bromo-4,6-difluorophenyl) | 14 | 76–81 (EtOH) | 1711 | 48.70 |
| 20 | 4-Acetylaminophenyl | CH$_2$—CH$_2$-(quinazoline-2,4-dione-3-yl) | 15 | 245–247 (MeCN) | 1714 | 38.22; 44.75 |
| 21 | 4-Tolyl | CH$_2$—CH$_2$-[4-(3-chlorophenyl)piperazin-1-yl] | 14 | 157–162 (EtOH) | 1704 | 45.71; 47.78; 52.78; 55.77 |
| 22 | 4-Chlorophenyl | CH$_2$—CH$_2$-[4-(3-chlorophenyl)piperazin-1-yl] | 11 | 166–168 (MeCN) | 1704 | 45.92; 47.75; 52.80; 55.80 |
| 23 | 4-Tolyl | CH$_2$—C(O)—NH—CH$_2$—Ph | 5 | 221–223 (EtOH) | 1685; 1718 | 42.27; 50.24 |

TABLE 1-continued

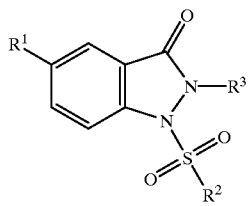

Formula VI $R^1 = CH_3O$

| Example | $R^2$ | $R^3$ | Yield (% of theory) | m.p. [° C.] | IR (KBr) [cm$^{-1}$] C=O | $^{13}$C—NMR (DMSO) N—CH$_2$ |
|---|---|---|---|---|---|---|
| 24 | 4-Tolyl | CH$_2$—NH—C(O)—C$_6$H$_4$—OCH$_3$ | 6 | 226–228 (EtOH) | 1690; 1704 | 51.31 |

Example 25

2-(2,6-Dichlorobenzoyl)-5-nitro-1-(toluene-4-sulphonyl)-1,2-dihydroindazol-3-one

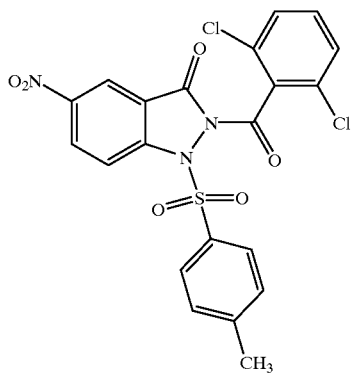

5 g (0.015 mol) of 5-nitro-1H-indazol-3-yl toluene-4-sulphonate are dissolved in 50 ml of pyridine and stirred at 80° C. for 30 minutes with 3.77 g (0.018 mol) of 2,6-dichlorobenzoyl chloride. After cooling, the mixture is stirred into 150 ml of water, treated with 100 ml of 5 N HCl, and the solid is filtered off with suction and washed with water. The crude product is purified by preparative HPLC using silica gel Si 60 and the eluent methylene chloride/ethyl acetate=99/1.

Yield: 2.4 g (32% of theory)

M.p. 195–197° C. (EtOAc)

$^{13}$C NMR (DMSO-d$_6$; 300 MHz): δ=20.27 CH$_3$; 159.33 C=O; 162.87 C=O.

IR(KBr): ν=1726 cm$^{-1}$ C=O.

Example 26

1-(3,4-Dichlorobenzyl)-2-(2-hydroxy-5-nitrobenzyl)-5-methylthio-1,2-dihydroindazol-3-one hydrate

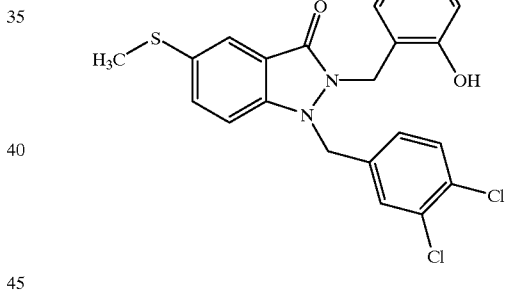

3.6 g (11 mmol) of 1-(3,4-dichlorobenzyl)-5-methylthio-1H-indazol-3-ol are dissolved in 100 ml of DMSO and treated in portions with 0.34 g (13.2 mmol) of sodium hydride (95 percent). After stirring for 2 hours, a solution of 2.1 g (11 mmol) of 2-hydroxy-5-nitrobenzyl chloride in 20 ml of DMSO is added dropwise and the mixture is stirred at 60° C. for 3 hours. After cooling, 200 ml of water are added dropwise, the mixture is stirred for 4 hours and the solid is filtered off with suction. The precipitate is extracted by stirring with methanol whilst hot and recrystallized from 2-propanol.

Yield: 1.0 g (18.5% of theory)

M.p. 225° C.

$^{13}$C NMR (DMSO-d$_6$; 300 MHz): δ=13.7 CH$_3$S; 48.8 2×CH$_2$N; 160.6 C=O.

IR(KBr): ν=1623 cm$^{-1}$ C=O.

The compound shown in Table 2 is prepared by an analogous procedure using 5-methoxy-1-(3-nitrobenzyl)-1H-indazol-3-ol as a starting substance.

TABLE 2

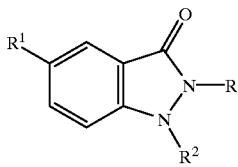

Formula VII $R^1 = CH_3O$

| Example | $R^2$ | $R^3$ | Yield (% of theory) | m.p. [° C.] | IR (KBr) [cm$^{-1}$] C=O | $^{13}$C—NMR (DMSO) N—CH$_2$ |
|---|---|---|---|---|---|---|
| 27 | 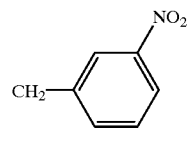 | 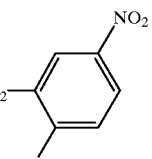 | 61 | 232 (MeCN) | 1642 | 40.51; 53.44 |

Example 28

5-Methoxy-1-(3-nitrobenzyl)-3-oxo-1,3-dihydroindazole-2-carboxylic acid (2-fluorophenyl)amide

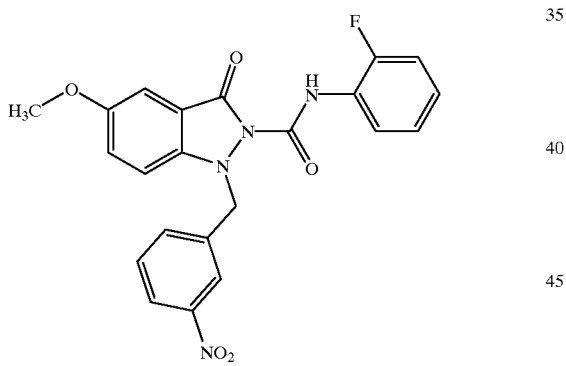

1.8 g (0.013 mol) of 2-fluorophenyl isocyanate are added to a solution of 3.0 g (0.01 mol) of 5-methoxy-1-(3-nitrobenzyl)-1H-indazol-3-ol in 100 ml of tetrahydrofuran and the mixture is heated under reflux for 4 hours. It is then concentrated to 20 ml, and the precipitate deposited is filtered off with suction and recrystallized from ethyl acetate.

Yield: 1.1 g (25% of theory)

M.p. 149–151° C.

$^{13}$C NMR (DMSO-d$_6$; 300 MHz): δ=157.22 C=O; 165.15 C=O.

IR(KBr): ν=1682; 1727 cm$^{-1}$ C=O.

The compounds listed in Table 3 are prepared by an analogous procedure.

TABLE 3
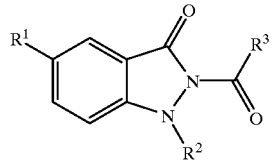
Formula VIII
$R^1 = CH_3O$
| Example | $R^2$ | $R^3$ | Yield (% of theory) | m.p. [° C.] | IR (KBr) [cm$^{-1}$] C=O | $^{13}$C—NMR (DMSO) C=O |
|---|---|---|---|---|---|---|
| 29 | 3-NO$_2$-C$_6$H$_4$-CH$_2$- | 2,6-Cl$_2$-C$_6$H$_3$-NH- | 31 | 170–172 (EtOAc) | 1684; 1730 | 156.77; 164.88 |
| 30 | 3-NO$_2$-C$_6$H$_4$-CH$_2$- | 2-CF$_3$-6-F-C$_6$H$_3$-NH- | 78 | 200–201 (EtOH) | 1693; 1732 | 155.21; 163.16 |
| 31 | 3-(CO$_2$CH$_3$)-C$_6$H$_4$-CH$_2$- | 2-F-C$_6$H$_4$-NH- | 49 | 149–154 (EtOH) | 1685; 1721 | 156.65; 164.95; 166.48 |
| 32 | 4-F-C$_6$H$_4$-CH$_2$- | 2,6-Cl$_2$-C$_6$H$_3$-NH- | 65 | 165 (MeCN) | 1695; 1736 | 156.43; 165.01 |
| 33 | 4-F-C$_6$H$_4$-CH$_2$- | 4-NO$_2$-C$_6$H$_4$-CH$_2$-O- | 8 | 156–158 (MeCN) | 1730 b | 157.05; 164.83 |
| 34 | 2-F-6-Cl-C$_6$H$_3$-CH$_2$- | 2,6-Cl$_2$-C$_6$H$_3$-NH- | 50 | 169–171 (EtOAc) | 1692; 1740 | 159.38; 168.14 |

TABLE 3-continued

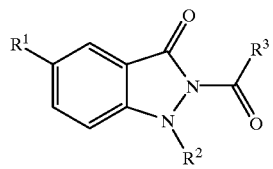

Formula VIII $R^1 = CH_3O$

| Example | $R^2$ | $R^3$ | Yield (% of theory) | m.p. [° C.] | IR (KBr) [cm$^{-1}$] C=O | $^{13}$C—NMR (DMSO) C=O |
|---|---|---|---|---|---|---|
| 35 | F-phenyl-Cl-CH$_2$- | 2,6-Cl$_2$-phenyl-NH- | 60 | 151–153 (EtOH) | 1687; 1737 | 156.79; 165.53 |

To determine the anti-asthmatic, anti-allergic, anti-inflammatory and/or immunomodulating properties of the compounds according to the invention, in vitro and in vivo investigations were carried out.

The compounds according to the invention as in formula I are surprisingly distinguished by immunophilin binding and inhibit its peptidyl-prolyl cis-trans-isomerase (PPIase) activity. For the initial screening (10 µmol/l), the inhibition of the human cyclophilin B in the PPIase test is determined. Assay for the determination of the peptidylprolyl isomerase (PPIase) activity and inhibition Method:

The PPIase activity is tested according to a globally customary enzyme test: G. Fischer, H. Bang, C. Mech, Biomed. Biochim. Acta 43 1101–1111; G. Fischer, H. Bang, A. Schellenberger, Biochim. Biophys. Acta 791 (1984), 87–97; D. H. Rich et al., J. Med. Chem. 38 (1995), 4164–4170.

The compounds of the general formula I according to the invention are preincubated at 4° C. for 15 minutes together with 10 nmol of Cyp B. The enzyme reaction is started using the test peptide Suc-Ala-Ala-Pro-Phe-Nan after addition of chymotrypsin and HEPES buffer. The extinction change at 390 nm is then monitored and evaluated. The photometrically determined extinction change results from two sub-reactions: a) the rapid chymotryptic cleavage of the trans-peptide; b) the non-enzymatic cis-trans isomerization, which is catalysed by cyclophilins. The determined inhibition of the PPIase activity of selected compounds of the general formula I is shown in Table 4:

TABLE 4

| Example | Inhibition of the PPIase activity at 10 µM |
|---|---|
| 1 | 70 |
| 2 | 50 |
| 3 | 93 |
| 4 | 90 |
| 5 | 67 |
| 26 | 98 |

Inhibition of late-phase eosinophilia 24 h after inhalational ovalbumin challenge in actively sensitized guinea-pigs Method:

The inhibition of pulmonary eosinophil infiltration by the substances is tested in an in vivo test on male Dunkin-Hartley guinea-pigs (200–250 g) sensitized against ovalbumin (OVA). The sensitization is carried out by means of two intraperitoneal injections of a suspension of 20 µg of OVA together with 20 mg of aluminium hydroxide as an adjuvant in 0.5 ml of physiological saline solution per animal on two successive days. 14 days after the second injection, the animals are pretreated with mepyramine maleate (10 mg/kg i.p.) in order to protect them from anaphylactic death. 30 minutes later, the animals are exposed for 30 sec in a plastic box to an OVA aerosol (0.5 mg/ml) which is generated by a nebulizer driven by compressed air (19.6 kPa) (allergen challenge). Control animals are nebulized with physiological saline solution. 24 hours after the challenge, the animals are anaesthetized with an overdose of ethylurethane (1.5 g/kg of body weight i.p.) and a bronchoalveolar lavage (BAL) is carried out with 2×5 ml of physiological saline solution. The BAL fluid is collected, centrifuged at 300 rpm for 10 min and the cell pellet is then resuspended in 1 ml of physiological saline solution. The eosinophils are stained using the Becton-Dickinson test kit (N. 5877) for eosinophils and counted in a Neubauer chamber. 2 control groups (nebulization with physiological saline solution and nebulization with OVA solution) are additionally included in each test.

The percentage inhibition of the eosinophilia of the test group treated with substance is calculated according to the following formula:

(A-C)-(B-C)/(A-C)×100=% inhibition

The test substances are administered intraperitoneally or orally as a suspension in 10% polyethylene glycol 300 and 0.5% strength 5-hydroxyethylcellulose 2 hours before allergen challenge. The control groups are treated with the vehicle according to the administration form of the test substance. The number of animals per control and test group is 3–10. The results are listed in Table 5:

TABLE 5

| Example | Dose [mg/kg] | Administration | Eosinophils million/animal $\bar{x} \pm s$ | | | Inhibition [%] |
|---|---|---|---|---|---|---|
| | | | A | B | C | |
| 1 | 2 × 30 | i.p. -2h/+4h | 1.89 ± 0.42 | 0.51 ± 0.25 | 0.55 ± 0.12 | 97 |

The compounds according to the invention are thus particularly suitable for the production of medicaments for the treatment of diseases which are connected with the suppression of immunological processes.

What is claimed is:

1. 1,2,5-trisubstituted 1,2-dihydroindazol-3-ones of formula (I)

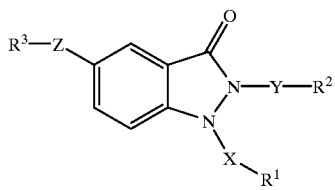

(I)

wherein

X is —SO$_2$—, —SO—, (CH$_2$)$_p$—, —(CH$_2$)$_p$—O—, —(CH$_2$)$_p$—(C=O)—, —(CH$_2$)$_p$—(C=O)—NH—, —(CH$_2$)$_p$—CHOH—, —CHOH—(CH$_2$)$_p$—, —(CH$_2$)$_p$—CH=CH—, —CH=CH—(CH$_2$)$_p$—,

Y is —(C=O)—, —(C=O)—NH—, —(C=O)—NH—(CH$_2$)$_p$—, —(C=O)—(CH$_2$)$_p$—, —(CH$_2$)$_p$—, —(CH$_2$)$_p$—(C=O)—, —(CH$_2$)$_p$—(C=O)—NH—, —(CH$_2$)$_p$—(C=O)—NH—(CH$_2$)$_p$—, —(CH$_2$)$_p$—CHOH—, —CHOH—(CH$_2$)$_p$—, —(CH$_2$)$_p$—CH=CH—, —CH=CH—(CH$_2$)$_p$—,

Z is —O—, —O—(CH$_2$)$_p$—, —NH—, —NH—(C=O)—, —NH—(C=O)—NH—, —NH—(C=O)—O—, —NH—CH$_2$—(C=O)— and —NH—(C=O)—CH$_2$—, P is a cardinal number from 1 to 4, R$^1$, R$^2$ and R$^3$ are the same or different and are:
mono-, bi- or tricyclic saturated or mono- or polyunsaturated carbocycles having from 5 to 14 ring members; or mono-, bi- or tricyclic saturated or mono- or polyunsaturated heterocycles having from 5 to 15 ring members and from 1 to 6 heteroatoms, in which the carbocycles and the heterocycles can be mono- or polysubstituted by:
—C$_{1-6}$-alkyl, —O—C$_{1-6}$-alkyl, —O—C$_{3-7}$-cycloalkyl, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, R$^1$ is also H, provided that when X is (CH$_2$)$_p$, then R$^1$ is not H, R$^3$—Z is also NO$_2$, and their pharmaceutically acceptable salts, but excluding compounds of formula (I) in which
if Z is —NH—(C=O)—, —NH—(C=O)—NH—, —NH—(C=O)—O—, —NH—(C=O)—CH$_2$— and at the same time R$^1$ is phenyl, monosubstituted or polysubstituted by —COOH, —COOC$_{1-6}$-alkyl, —(CH$_2$)$_p$—COOH, —(CH$_2$)$_p$—COOC$_{1-6}$-alkyl —CONHC$_{1-6}$-alkyl, —CONHC$_{6-14}$-aryl, —CONHSO$_2$C$_{1-6}$-alkyl, —CONHSO$_2$C$_{6-14}$-aryl, 1H-tetrazol-5-yl, then R$^2$ is not phenyl, monosubstituted or polysubstituted by CN, halogen, C$_{1-4}$-alkyl, C$_{1-4}$-alkyloxy, CF$_3$; and if R$^3$—Z is NO$_2$, then R$^1$—X is not benzyl or 4-methoxybenzyl, and R$^2$—Y is not benzyl or 2-picolyl at the same time.

2. The compounds of claim 1, wherein in R$^1$, R$^2$, and R$^3$ said carbocycles of 5 to 14 ring members, are one or more of phenyl, napthyl, anthranyl, and fluorenyl; and wherein in R$^1$, R$^2$, and R$^3$ said heteroatoms are N, O, or S; and wherein said heteroatoms mono- or polysubstituting said carbocycles and heterocycles are N, O, S, —F, —Cl, —Br, —I, —OH, —SH, —O$_2$, —NH$_2$, —NHC$_{1-6}$-alkyl, —N(C$_{1-6}$-alkyl)$_2$, —NHC$_{6-14}$-aryl, —N(C$_{6-14}$-aryl)$_2$, —N(C$_{1-6}$-alkyl)(C$_{6-14}$-aryl), —NHCOC$_{1-6}$-alkyl, —NHCOC$_{6-14}$-aryl, —CONHC$_{1-6}$-alkyl, —CONHC$_{6-14}$-aryl, —CONHSO$_2$C$_{1-6}$-alkyl, —CONHSO$_2$C$_{6-14}$-aryl, —CN, —(CO)C$_{1-6}$-alkyl, —(CS)C$_{1-6}$-alkyl, —COOH, —COOC$_{1-6}$-alkyl, —O—C$_{6-14}$-aryl, —O—(CO)C$_{1-6}$-alkyl, —O—(CO)C$_{6-14}$-aryl, benzyl, benzyloxy, —S—C$_{1-6}$-alkyl, —S—C$_{6-14}$-aryl, —CF$_3$, —(CH$_2$)$_p$—COOH, —(CH$_2$)$_p$—COOC$_{1-6}$-alkyl —SO$_2$—C$_{1-6}$-alkyl or —SO$_2$-C$_{6-14}$-aryl.

3. The compounds of claim 2, wherein when R$^1$, R$^2$, and/or R$^3$ is a heterocycle, then such heterocycle is thiophenyl, pyridinyl, isoxazolyl, benzimidazolyl, benzo[1,3]dioxolyl, pyrimidinyl, quinolyl, quinazolinyl, morpholinyl, pyrrolidinyl, pyrrolyl, benz[1,2,4]oxadiazolyl, benzothiazolyl.

4. A Compound of claim 1, being
2-(2-hydroxy-5-nitrobenzyl)-5-methoxy-1-(4-methoxybenzenesulfonyl)-1,2-dihydroindazol-3-one;
2-(2-hydroxy-5-nitrobenzyl)-5-methoxy-1-(toluene-4-sulfonyl)-1,2-dihydroindazol-3-one;
2-(2-hydroxy-5-nitrobenzyl)-5-methoxy-1-(4-trifluoromethoxybenzenesulfonyl)-1,2-dihydroindazol-3-one;
2-(2-hydroxy-5-nitrobenzyl)-5-methoxy-1-(4-chlorobenzenesulfonyl)-1,2-dihydroindazol-3-one;
1-(4-fluorobenzenesulfonyl)-2-(2-hydroxy-5-nitrobenzyl)-5-methoxy-1,2-dihydroindazol-3-one;
N-(4-[2-(2-hydroxy-5-nitrobenzyl)-5-methoxy-3-oxo-2,3-dihydroindazol-1-sulfonyl]phenyl)acetamide;
2-(4-fluorobenzyl)-5-methoxy-1-(toluene-4-sulfonyl)-1,2-dihydroindazol-3-one;
2-(4-fluorobenzyl)-5-methoxy-1-(4-chlorobenzenesulfonyl)-1,2-dihydroindazol-3-one;
1-(4-fluorobenzenesulfonyl)-2-(4-fluorobenzyl)-5-methoxy-1,2-dihydroindazol-3-one;
2-(2-fluorobenzyl)-5-methoxy-1-(toluene-4-sulfonyl)-1,2-dihydroindazol-3-one;
1-(4-fluorobenzenesulfonyl)-2-(2-fluorobenzyl)-5-methoxy-1,2-dihydroindazol-3-one;
2-(3-methoxybenzyl)-5-methoxy-1-(toluene-4-sulfonyl)-1,2-dihydroindazol-3-one;
2-(3-trifluoromethylbenzyl)-5-methoxy-1-(toluene-4-sulfonyl)-1,2-dihydroindazol-3-one;
2-[2-(4-chlorophenyl)thiazol-4-ylmethyl]-5-methoxy-1-(toluene-4-sulfonyl)-1,2-dihydroindazol-3-one;
5-methoxy-2-(3-phenylallyl)-1-(toluene-4-sulfonyl)-1,2-dihydroindazol-3-one;
5-methoxy-2-(3-oxo-3-phenylpropyl)-1-(toluene-4-sulfonyl)-1,2-dihydroindazol-3-one;
2-[2-(2,6-difluorophenoxy)ethyl]-5-methoxy-1-(toluene-4-sulfonyl)-1,2-dihydroindazol-3-one;
2-[2-(2-bromo-4,6-difluorophenoxy)ethyl]-5-methoxy-1-(toluene-4-sulfonyl)-1,2-dihydroindazol-3-one;

2-[2-(2-bromo-4,6-difluorophenoxy)ethyl]-5-methoxy-1-(4-methoxybenzenesulfonyl)-1,2-dihydroindazol-3-one;
N-(4-{2-[2-(2,4-dioxo-1,4-dihydro-2H-quinazolin-3-yl)ethyl]-5-methoxy-3-oxo-2,3-dihydroindazol-1-sulfonyl}phenyl)acetamide;
2-{3-[4-(3-chlorophenyl)piperazin-1-yl]propyl}-5-methoxy-1-(toluene-4-sulfonyl)-1,2-dihydroindazol-3-one;
1-(4-chlorobenzenesulfonyl)-2-{3-[4(3-chlorophenyl)piperazin-1-yl]propyl}-5-methoxy-1-(toluene-4-sulfonyl)-1,2-dihydroindazol-3-one;
N-benzyl-2-[5-methoxy-3-oxo-1-(toluene-4-sulfonyl)-1,3-dihydroindazol-2-yl]acetamide;
2-[5-methoxy-3-oxo-1-(toluene-4-sulfonyl)-1,3-dihydroindazol-2-yl]-N-(4-methoxyphenyl)-acetamide;
2-(2,6-dichlorobenzoyl)-5-nitro-1-(toluene-4-sulfonyl)-1,2-dihydroindazol-3-one;
1-(3,4-dichlorobenzyl)-2-(2-hydroxy-5-nitrobenzyl)-5-methylthio-1,2-dihydroindazol-3-one;
2-(2-hydroxy-5-nitrobenzyl)-5-methoxy-1-(3-nitrobenzyl)-1,2-dihydroindazol-3-one;
5-methoxy-1-(3-nitrobenzyl)-3-oxo-1,3-dihydroindazol-2-carboxylic acid (2-fluorophenyl)amide;
5-methoxy-1-(3-nitrobenzyl)-3-oxo-1,3-dihydroindazol-2-carboxylic acid (2,6-dichlorophenyl)amide;
5-methoxy-1-(3-nitrobenzyl)-3-oxo-1,3-dihydroindazol-2-carboxylic acid (2-fluoro-6-trifluoromethylphenyl)amide;
methyl 3-[2-(2-fluorophenylcarbamoyl)-5-methoxy-3-oxo-2,3-dihydroindazol-1-ylmethyl]-benzoate;
1-(4-fluorobenzyl)-5-methoxy-3-oxo-1,3-dihydroindazole-2-carboxylic acid (2,6-dichlorophenyl)amide;
4-nitrobenzyl 1-(4-fluorobenzyl)-5-methoxy-3-oxo-1,3-dihydroindazole-2-carboxylate;
1-(2,6-difluorobenzyl)-5-methoxy-3-oxo-1,3-dihydroindazole-2-carboxylic acid (2,6-dichlorophenyl) amide; and
1-(2-chloro-6-fluorobenzyl)-5-methoxy-3-oxo-1,3-dihydroindazole-2-carboxylic acid (2,6-dichlorophenyl) amide.

5. The pharmaceutically acceptable salts of claim 1, obtained by (i) neutralization of the bases with inorganic or organic acids, (ii) neutralization of the acids with inorganic or organic bases, or (iii) quaternization of a tertiary amine to give a quaternary ammonium salt.

6. A process for the treatment of diseases mediated by PPIase, which comprises admninistering to a patient in need therefor a pharmaceutical composition containing as active ingredient the compound or salt of claim 1.

7. An immunomodulating, antiasthmatic, antiallergic, antiinflammatory process which comprises admninistering to a patient in need therefor a pharmaceutical composition containing as active ingredient the compound or salt of claim 1.

8. A process for preparing a compound of claim 1, which comprises
a) when X is —$SO_2$—, —SO—, reacting a 1H-indazol-3-yl sulfonate of formula (II)

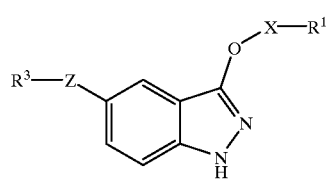

(II)

in the presence of a base and optionally in the presence of a diluent to provide a compound of formula (III)

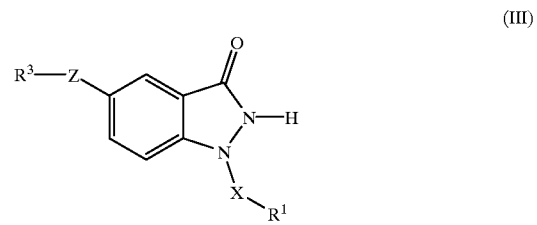

(III)

where $R^1$, $R^3$, X and Z have the same meaning, and reacting 1H-indazol-3-yl sulfonate of formula (II), or a 1-sulfonylindazole of formula (III), optionally in the presence of a base, and in the optional presence of a diluent, with a compound of the formula Hal-Y-$R^2$, O=C=N—$(CH_2)_p$—$R^2$, or [$R^2$—$(CH_2)_p$—C=O]$_2$O where $R^1$, $R^2$, $R^3$, X, Y and Z have the same meanings, and Hal is a halogen atom, to provide a compound of formula (I); or (b) when X is —$(CH_2)_p$—, —$(CH_2)_p$—O—, —$(CH_2)_p$—(C=O)—, —$(CH_2)_p$—(C=O)—NH—, —$(CH_2)_p$—CHOH—, —CHOH—$(CH_2)_p$—, —$(CH_2)_p$—CH=CH—, —CH=CH—$(CH_2)_p$— reacting a compound of formula (III), optionally in the presence of a base, and in the optional presence of a diluent with a compounds of the formula Hal-Y-$R^2$, O=C=N—$(CH_2)_p$—$R^2$, or [$R^2$—$(CH_2)_p$—C=O]$_2$O, where $R^1$, $R^2$, $R^3$, X, Y and Z have the same meaning and Hal is a halogen atom, to provide a compound of formula (I), (c) where the compound of formula (III) can also be present as the tautomeric form formula IV

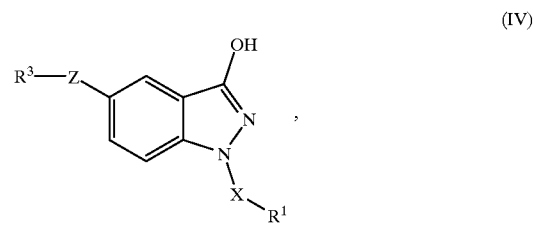

(IV)

9. The process of claim 8, wherein in (a) the optional base is sodium hydride, and the optional diluent is dimethyl sulfoxide; and in (b) the optional base is pyridine, or sodium hydride, and the optional diouent is dimethyl solfoxide, or tetrahydrofuran.

10. A pharmaceutical composition containing at least one compound of claim 11 as active ingredient, together with a pharmaceutically acceptable carrier and/or diluents or auxiliary.

11. The pharmaceutical composition of claim 10, when in the form of a coated or uncoated tablet, capsule, aerosol, powder formulation, patch, solution, ampoule, or suppository.

12. A 1,2,5-trisubstituted 1,2-dihydroindazol-3-one of formula (1)

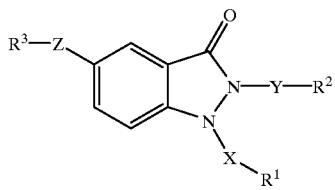
(I)

wherein
- X is —SO$_2$—, or —(CH$_2$)$_p$;
- Y is —(CH$_2$)$_p$—, (CH$_2$)$_p$—CH=CH—, —(CH$_2$)$_p$—(C=O)—, (CH$_2$)$_p$—(C=O)—NH—, —(C=O)—, —(C=O)—NH, or —(C=O)—O—(CH$_2$)$_p$—;
- Z is —O—, or —S—;
- R$^1$ is phenyl, optionally mono -or -polysubstituted with COOC$_{1-6}$ alkyl, C$_{1-6}$ alkoxy, trifluoromethoxy, halogen, C$_{1-6}$-alkanoylamino, —NO$_2$, or COOC$_{1-6}$-alkyl;
- R$^2$ is phenyl, optionally mono -or -polysubstituted with —NO$_2$, —OH, halogen, C$_{1-6}$alkoxy, trifluoromethoxy, trifluoromethyl, or with formula (V)

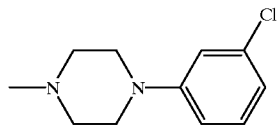
(V)

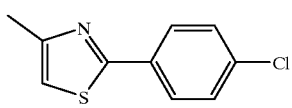

- R$^3$ is C$_{1-6}$ alkyl;
- R$^3$—Z is —NO$_2$;
- p is a cardinal number from 1 to 4; and their pharmaceutically acceptable salts, provided that when R$^3$—Z is NO$_2$, then R$^1$—X and R$^2$—Y cannot be simultaneously R$^1$—X=benzyl, or 4-methoxybenzyl, and R$^2$—Y=benzyl, or picolyl.

* * * * *